(12) United States Patent
Chan (10) Patent No.: US 9,651,502 B2
(45) Date of Patent: May 16, 2017

(54) METHOD AND SYSTEM FOR DETECTING MICRO-CRACKS IN WAFERS

(75) Inventor: Sok Leng Chan, Singapore (SG)

(73) Assignee: BLUPLANET PTE LTD, Singapore (SG)

(*) Notice: Subject to any disclaimer, the term of this patent is extended or adjusted under 35 U.S.C. 154(b) by 1225 days.

(21) Appl. No.: 12/681,717

(22) PCT Filed: May 14, 2009

(86) PCT No.: PCT/SG2009/000173
§ 371 (c)(1),
(2), (4) Date: Apr. 5, 2010

(87) PCT Pub. No.: WO2010/014041
PCT Pub. Date: Feb. 4, 2010

(65) Prior Publication Data
US 2010/0220186 A1    Sep. 2, 2010

(30) Foreign Application Priority Data
Jul. 28, 2008  (SG) .............................. 200805811-7

(51) Int. Cl.
*H04N 7/18* (2006.01)
*G01N 21/95* (2006.01)
(Continued)

(52) U.S. Cl.
CPC ......... *G01N 21/9505* (2013.01); *G01N 21/88* (2013.01); *G01N 21/956* (2013.01);
(Continued)

(58) Field of Classification Search
CPC ........ H04N 7/18; G01N 21/88; G01N 21/956; G01R 31/309
(Continued)

(56) References Cited

U.S. PATENT DOCUMENTS 6,088,470 A * 7/2000 Camus et al. ................ 382/117
6,829,047 B2  12/2004 Fujii et al.
(Continued)

FOREIGN PATENT DOCUMENTS

JP   2003-017536 A   1/2003
JP   2004-317470 A   11/2004
(Continued)

OTHER PUBLICATIONS

Office Action mailed Aug. 2, 2012 in co-pending U.S. Appl. No. 12/681,722.
(Continued)

*Primary Examiner* — Shawn An
(74) *Attorney, Agent, or Firm* — Nields, Lemack & Frame, LLC (57) ABSTRACT

An inspection method comprises receiving light emanating from a first surface of a wafer substantially along a first axis for obtaining a first image of the first surface therefrom, the wafer having a crack formed therein and the first image containing at least one portion of the crack. The inspection method also comprises receiving light emanating from the first surface of the wafer substantially along a second axis for obtaining a second image of the first surface therefrom, the second image containing at least one second portion of the crack, the first surface extending substantially parallel a plane, and the orthographic projection of the first axis on the plane being substantially perpendicular the orthographic projection of the second axis on the plane. The inspection method further comprises constructing a third image from the at least one first portion of the crack and the least one second portion of the crack of the first and second images respectively. More specifically, the third image is substantially processable for inspecting the crack in the wafer.

25 Claims, 6 Drawing Sheets

(51) Int. Cl.
*G01N 21/88* (2006.01)
*G01N 21/956* (2006.01)
*H01L 21/66* (2006.01)
*G01R 31/309* (2006.01)
*H01L 31/18* (2006.01)

(52) U.S. Cl.
CPC ............... *H01L 22/12* (2013.01); *H04N 7/18* (2013.01); *G01R 31/309* (2013.01); *H01L 31/18* (2013.01); *H01L 2924/0002* (2013.01)

(58) Field of Classification Search
USPC .................. 348/125–126, 133–134, 131
See application file for complete search history.

(56) References Cited

U.S. PATENT DOCUMENTS

| | | | |
|---|---|---|---|
| 6,891,570 B2* | 5/2005 | Tantalo et al. | 348/362 |
| 7,283,224 B1 | 10/2007 | Smithgall | |
| 7,667,834 B2* | 2/2010 | Clasen | 356/237.1 |
| 7,801,357 B2* | 9/2010 | Yoshiura et al. | 382/167 |
| 8,077,305 B2 | 12/2011 | Owen et al. | |
| 8,149,376 B2 | 4/2012 | Ohashi | |
| 2006/0278831 A1 | 12/2006 | Matsumoto et al. | |
| 2007/0009148 A1* | 1/2007 | Brasen et al. | 382/149 |
| 2007/0188610 A1* | 8/2007 | Micotto et al. | 348/144 |
| 2007/0262002 A1 | 11/2007 | Ito et al. | |
| 2007/0263206 A1 | 11/2007 | LeBlanc et al. | |
| 2010/0074516 A1* | 3/2010 | Kawaragi | G01N 21/956 382/149 |
| 2010/0177191 A1 | 7/2010 | Stier | |
| 2011/0268344 A1 | 11/2011 | Chan | |

FOREIGN PATENT DOCUMENTS

| | | |
|---|---|---|
| JP | 2007-147547 A | 6/2007 |
| JP | 2007-218638 A | 8/2007 |
| JP | 2008-267851 A | 11/2008 |
| KR | 10-1994-0020481 A | 9/1994 |
| WO | 2005/100961 | 10/2005 |
| WO | 2007/041758 | 11/2007 |

OTHER PUBLICATIONS

International Search Report dated Dec. 21, 2009 in corresponding foreign application (PCT/SG2009/000173).
International Search Report dated Dec. 7, 2009 in foreign application (PCT/SG2009/000174).
Notice of Allowance mailed Feb. 14, 2013 in co-pending U.S. Appl. No. 12/681,722.
Notice of Allowance mailed Oct. 31, 2012 in co-pending U.S. Appl. No. 12/681,722.

* cited by examiner

METHOD AND SYSTEM FOR DETECTING MICRO-CRACKS IN WAFERS

FIELD OF INVENTION

The present invention generally relates to apparatuses and methods for inspection of an object. In particular, the invention relates to an apparatus and a method for inspecting wafers for defects.

BACKGROUND

Solar cells manufacturers routinely perform inspection on their solar wafers. This is to ensure that any defective solar wafers are identified so as to control the quality of the solar cells.

A solar wafer is a thin slice of silicon crystal that is commonly used in the fabrication of solar cells. A solar wafer serves as a substrate for solar cells and undergoes a series of fabrication processes, for example deposition, etching and patterning, before becoming a functional solar cell. It is therefore very critical to maintain the quality of solar wafers from the beginning of the fabrication processes in order to improve production yield and reduce production cost.

Micro-crack is a common defect found in solar wafers, which is extremely difficult to detect because some micro-cracks are invisible to the human eyes and even to optical microscopes. One method of detecting micro-cracks in solar wafers involves the use of infrared imaging technique. Solar wafers are made from silicon of high purity and appear opaque under visible light. However, due to silicon's band-gap energy level, solar wafers appear transparent when illuminated with light having a wavelength larger than 1127 nm.

Light having a wavelength of 1127 nm is classified as near infrared (NIR) radiation. NIR is invisible to the human eye but is detectable by most commercial CCD or CMOS infrared cameras. Examples of infrared light sources are Light Emitting Diodes (LED), tungsten lamp and halogen lamp.

As infrared light is capable of penetrating through a solar wafer made from silicon, it is possible to examine the internal structure of the solar wafer by displacing the solar wafer in between the infrared camera and light source.

Solar wafers are manufactured in a production line at high volume, typically at a rate of one wafer per second. A solar wafer typically has a rectilinear shape and a surface dimension of between 100 mm by 100 mm and 210 mm by 210 mm. The solar wafer also has a typical thickness of between 150 μm to 250 μm. A conventional high speed imaging system is used for inspecting the solar wafers. Most conventional high speed imaging system uses a line-scan CCD/CMOS camera that has a resolution of up to 12000 (12K) pixels.

Figure 1A:
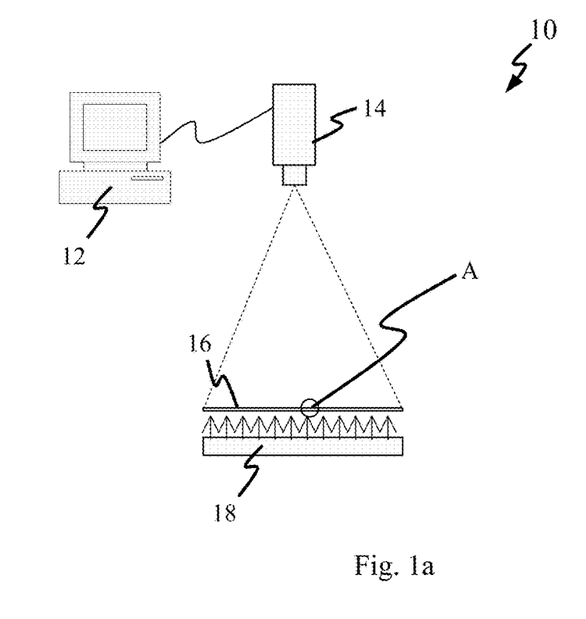
FIG. 1a shows a conventional system for inspecting a solar wafer and FIG. 1b is an enlarged cross-sectional view of the solar wafer.

FIG. 1a shows a conventional high speed imaging system 10. The conventional high speed imaging system 10 consists of a computer 12 and a line-scan imaging device 14. The line-scan imaging device 14 includes cameras and a lens system and is positioned above a solar wafer 16 perpendicularly to its surface. An infrared light source 18 is placed below the solar wafer 16 such that infrared light penetrates the solar wafer 16 and reaches the line-scan imaging device 14.

To inspect a 210 mm by 210 mm solar wafer, a 12K line-scan camera is required to have an image resolution better than 210 mm/12,000 pixels or 18 μm/pixel. Based on sampling theorem, this image resolution is only useful for detecting micro-cracks having a crack line width of more than 2 pixels. This means that conventional high speed imaging systems are limited to detecting micro-cracks that has a crack line width larger than 2 pixels×18 μm/pixel or 36 μm. This is a major limitation to conventional high speed imaging systems because the width of micro-cracks is typically smaller than 36 μm.

Figure 1B:
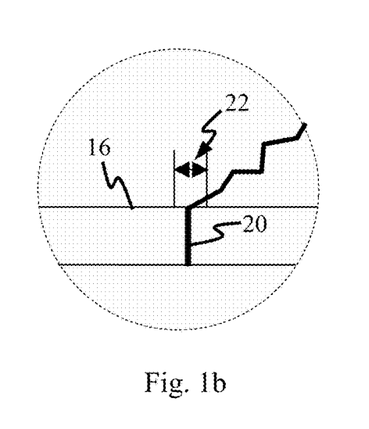

FIG. 1b shows a close-up view of a micro-crack 20 along a cross-section of the solar wafer 16 at point A of FIG. 1a. The micro-crack 20 has a width smaller than the image resolution 22 of the conventional high speed imaging system 10. As a result, output images of the micro-crack 20 do not have sufficient contrast to allow image analysis software to detect the micro-crack 20.

Figure 2:
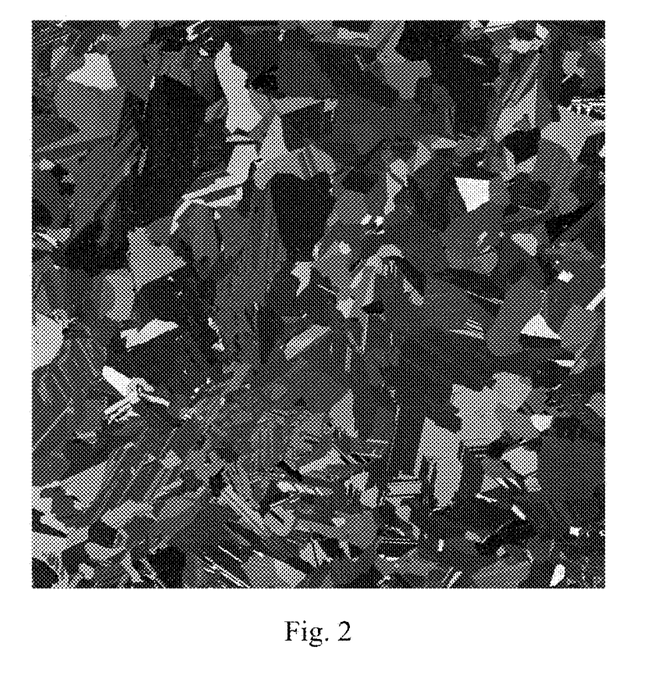
FIG. 2 shows a multi-crystalline structure of a solar wafer.

Other than image resolution problem, detecting micro-crack in solar wafers becomes more complicated when the solar wafer is of multi-crystalline type. Solar wafers are typically fabricated from mono-crystalline or multi-crystalline wafers. Mono-crystalline solar wafers are typically made by cutting single-crystal silicon into slices. Multi-crystalline solar wafers, on the other hand, are obtained by melting a pot of silicon and then allowed the melted silicon to cool slowly before cutting the solidified silicon into slices. Although multi-crystalline solar wafers are lower in quality than mono-crystalline solar wafers due to higher impurity level in the silicon, multi-crystalline solar wafers are nonetheless more cost effective and are becoming more widely used than mono-crystalline solar wafer for making solar cells. Mono-crystalline solar wafers appear to have a uniform surface texture. As shown in FIG. 2, multi-crystalline solar wafers exhibit complicated random surface texture due to the formation of crystal grains of varied size during the solidification process.

The random surface texture in multi-crystalline solar wafers also appears in the output images of the conventional high speed imaging systems 10. Crystal grain boundaries and the contrast between different crystal grains increase the difficulty in detecting the micro-cracks.

There is therefore a need for an improved system and method for facilitating detection of micro-cracks in wafers.

SUMMARY

Embodiments of the invention disclosed herein involve an improved system and method for facilitating detection of micro-cracks in wafers.

Therefore, in accordance with a first embodiment of the invention, there is disclosed an inspection method. An inspection method comprises receiving light emanating from a first surface of a wafer substantially along a first axis for obtaining a first image of the first surface therefrom, the wafer having a crack formed therein and the first image containing at least one portion of the crack. The inspection method also comprises receiving light emanating from the first surface of the wafer substantially along a second axis for obtaining a second image of the first surface therefrom, the second image containing at least one second portion of the crack, the first surface extending substantially parallel a plane, and the orthographic projection of the first axis on the plane being substantially perpendicular the orthographic projection of the second axis on the plane. The inspection method further comprises constructing a third image from the at least one first portion of the crack and the least one second portion of the crack of the first and second images respectively. More specifically, the third image is substantially processable for inspecting the crack in the wafer.

In accordance with a second embodiment of the invention, there is disclosed an inspection apparatus comprising a light assembly disposed for directing light towards a first surface of a wafer, the wafer having a crack formed therein. The inspection apparatus also comprises a first imaging device disposed for receiving light emanating substantially along a first axis from a second surface of the wafer wherefrom a first image containing at least one first portion of the crack is obtainable, the second surface being substantially parallel a plane and substantially outwardly opposing the first surface. The inspection apparatus further comprises a second imaging device disposed for receiving the light emanating substantially along a second axis from the second surface of the wafer wherefrom a second image containing at least one second portion of the crack is obtainable. The first and second imaging devices are inter-configured for disposing the orthographic projection of the first axis on the plane substantially perpendicular the orthographic projection of the second axis on the plane and data couplable with a computer to enable obtaining of the first and second images thereby. More specifically, a third image is constructible from the first and second images by the computer and subsequently processable for inspecting the crack in the wafer.

BRIEF DESCRIPTION OF THE DRAWINGS

Embodiments of the invention are disclosed hereinafter with reference to the drawings, in which.

DETAILED DESCRIPTION

With reference to the drawings, embodiments of the invention relate to creating a high contrast image of solar wafers for inspection purposes to facilitate detection of micro-cracks thereon.

Conventional methods and systems of creating images of solar wafers do not produce an image that has sufficiently high contrast for detecting minute micro-cracks on the solar wafers. Furthermore, the increasing utilization of multi-crystalline wafers for fabricating solar cells has raised the difficulty of detecting the minute micro-cracks using the foregoing conventional methods and systems.

For purposes of brevity and clarity, the description of the invention is limited hereinafter to applications related to an improved system and method for facilitating detection of micro-cracks in wafers used for fabricating solar cells. This however does not limit or preclude embodiments of the invention from other areas of application that facilitates inspection of other wafer types for defects detection. The fundamental inventive principles and concepts upon which embodiments of the invention are based shall remain common throughout the various embodiments.

An exemplary embodiment of the invention is described in greater detail hereinafter in accordance to illustrations provided in FIGS. 3 to 10 of the drawings, wherein like elements are identified with like reference numerals.

A method and apparatus for wafer inspection is described hereinafter for addressing the foregoing problems. The method and apparatus is suitable for inspecting solar wafers, as well as other wafer types such as semiconductor bare wafers or processed wafer that are used in the fabrication of integrated circuit chips.

Figure 3:
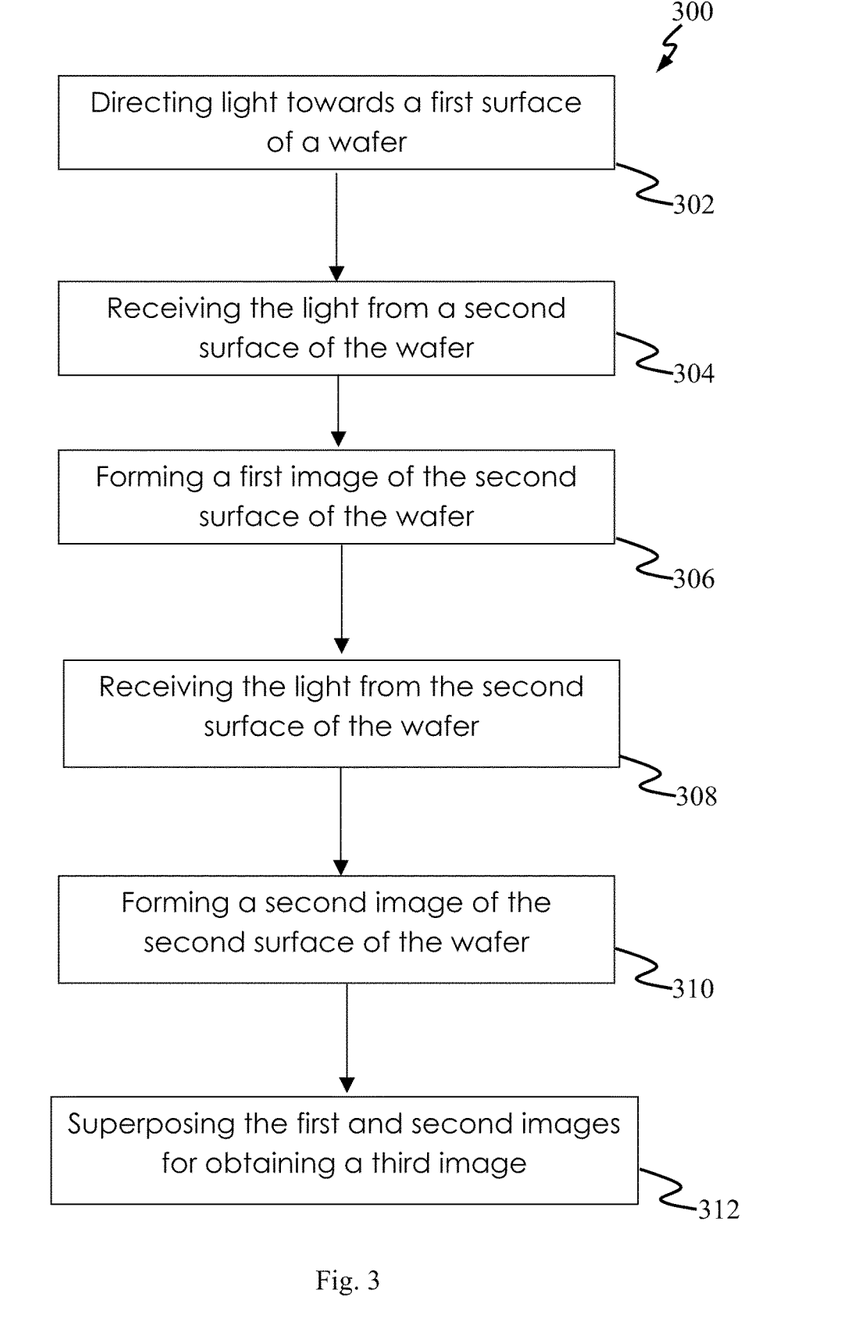
FIG. 3 is an inspection method according to a first embodiment of the invention.

FIG. 3 shows a flow diagram of a method 300 for inspecting a wafer, for instant a solar wafer, according to an exemplary embodiment of the invention. Defects such as micro-cracks in solar wafers typically extend between two outward facing surfaces, namely a first surface and a second surface of the solar wafer. The method 300 comprises a step 302 of directing infrared light towards the first surface of the solar wafer at an acute angle to the surface of the wafer. The first surface of the solar wafer is the lower side of the solar wafer.

The method 300 also comprises a step 304 of receiving the infrared light from a second surface of the solar wafer along a first direction, where the second surface of the solar wafer substantially outwardly opposes the first surface of the solar wafer. The second surface of a solar wafer is the upper side of the wafer.

The method 300 further comprises a step 306 of forming a first image of the second surface of the solar wafer based on infrared light received from the second surface of the wafer along the first direction.

The method yet further comprises a step 308 of receiving the infrared light from the second surface of the wafer along a second direction. In particular, the orthographic projection of the first direction on the first or second surface of the solar wafer is substantially perpendicular the orthographic projection of the second direction on the first or second surface of the solar wafer.

The method 300 then comprises a step 310 of forming a second image of the second surface of the solar wafer based on infrared light received from the second surface of the wafer along the second direction. The method 300 then further comprises a step 312 of superposing the first and second images for obtaining a third image, wherein the third image is processable for inspecting the wafer to thereby identify defects on the solar wafer.

Figure 4:
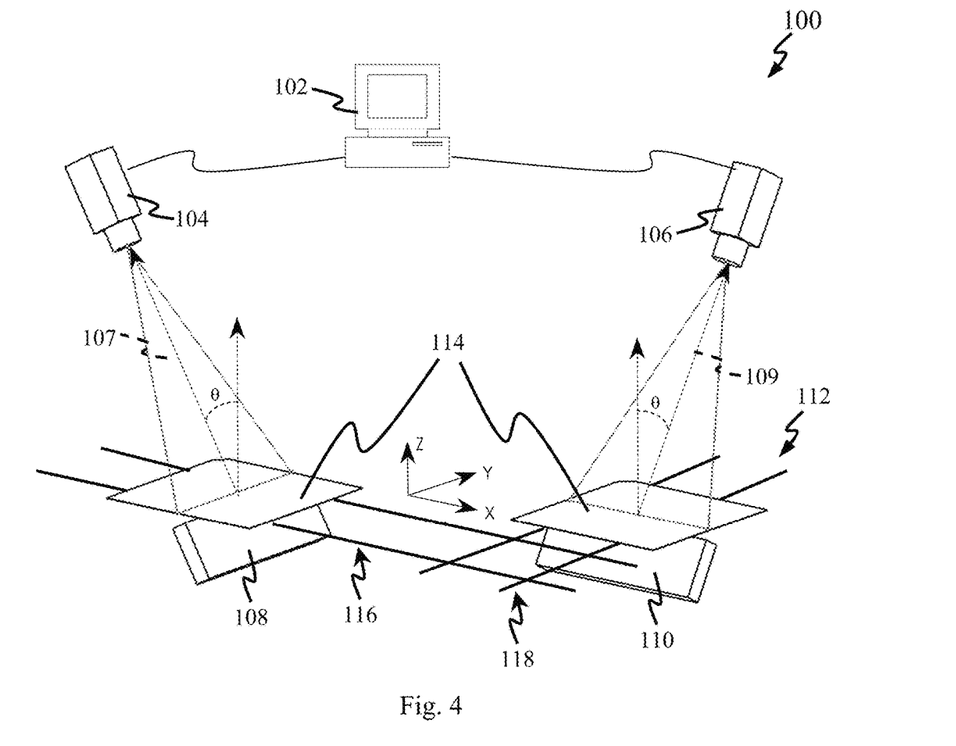
FIG. 4 is an inspection apparatus according to a second embodiment of the invention.

In accordance with an exemplary embodiment of the invention, an apparatus 100 for inspection is described with reference to FIG. 4, which shows a perspective view of the apparatus 100 according to a first embodiment of the invention. The apparatus 100 is preferably for implementing the foregoing method 300 for inspecting a solar wafer. The following description of the apparatus 100 is made with reference to an x-axis, a y-axis and a z-axis of a three-dimensional coordinate system. The x and y axes extend along a plane on which solar wafers are conveyed and are coincident therewith.

The apparatus 100 comprises a computer 102 and a first imaging device 104 and a second imaging device 106. The first and second imaging devices 104, 106 are preferably line-scan imaging cameras and are connected to the computer 102. Images captured by the first and second imaging devices 104, 106 are sent to the computer 102 for image analysis.

The apparatus 100 further comprises a light assembly that includes a first light source 108 and a second light source 110. The first and second light sources 108, 110 preferably emit infrared light that is detectable by the first and second imaging devices 104, 106. Specifically, the first and second light sources 108, 110 are positioned with respect to the first and second imaging devices 104, 106 for directing infrared light towards the first and second imaging devices 104, 106 respectively.

A conveyor system 112 is used for transporting solar wafers 114 for inspection by the apparatus 100. The conveyor system 112 has a first portion 116 and a second portion 118. The first portion 116 of the conveyor system 112 conveys a substantially planar solar wafer 114 linearly along the x-axis while the second portion 118 of the conveyor system 112 conveys the solar wafer 114 linearly along the y-axis. The solar wafer 114 is therefore conveyed substantially on the x-y plane.

More specifically, the first portion 116 of the conveyor system 112 is displaced in between the first imaging device 104 and the first light source 108 while the second portion 118 of the conveyor system 112 is displaced in between the second imaging device 106 and the second light source 110.

As the first portion 116 of the conveyor system 112 conveys the solar wafer 114 along the x-axis, the first light source 108 emits and substantially directs infrared light towards the lower surface of the solar wafer 114 at an acute angle θ. The first imaging device 104 is configured with respect to the z-axis normal to the solar wafer 114 for capturing infrared light emitted from the first light source 108 along the first direction 107. In this way, the apparatus 100 is able to capture and provide a first image of the solar wafer 114 along the x-axis.

Similarly, as the second portion 118 of the conveyor system 112 receives the solar wafer 114 from the first portion and conveys the solar wafer 114 along the y-axis, the second light source 110 emits and substantially directs infrared light towards the lower surface of the solar wafer 114 at the acute angle θ. The second imaging device 106 is configured with respect to the z-axis normal to the solar wafer 114 for capturing infrared light emitted from the first light source 108 along the second direction 109. In this way, the apparatus 100 is able to capture and provide a second image of the solar wafer 114 along the y-axis. In particular, the orthographic projection of the first direction 107 on the x-y plane is substantially perpendicular the orthographic projection of the second direction 109 on the x-y plane.

Figure 5A:
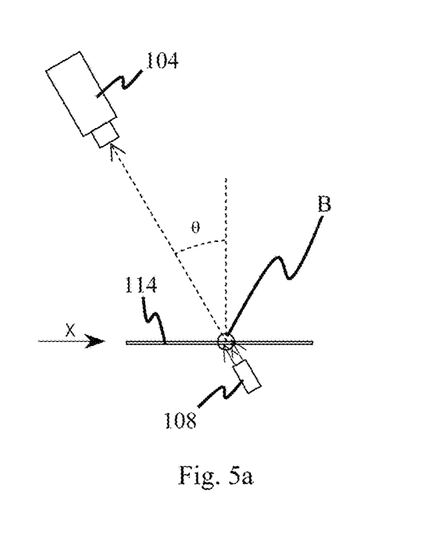
FIG. 5a is a side view of the apparatus of FIG. 4 along the x-axis and FIG. 5b is an enlarged cross-sectional view of a solar wafer.
Figure 5B:
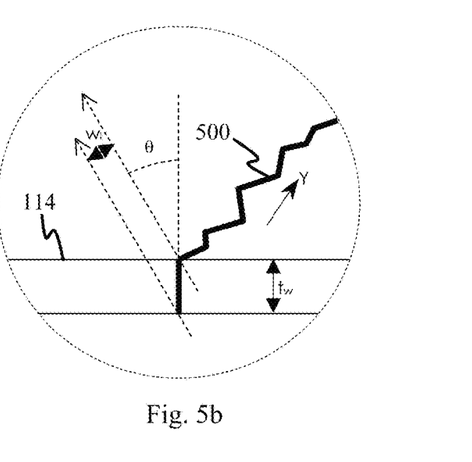

With reference to FIG. 5a, the oblique arrangement of the first and second imaging devices 104, 106 with respect to the first and second light sources 108, 110, allows images captured by the apparatus 100 to show highly contrasted micro-cracks 500. FIG. 5b is an enlarged cross-sectional view of the solar wafer 114 at point B of FIG. 5a. The micro-cracks 500 extend along the x and y axes against the upper surface of the solar wafer 114.

Mathematically, the width $w_i$ of the micro-cracks 500 in the images captured by the apparatus 100 is a function of the wafer thickness $t_w$ and the acute angle θ, according to the following mathematical relationship:

$$w_i = t_w \times \sin\theta$$

For example, the solar wafer 114 typically has a thickness of 200 μm. If the acute angle θ is 30°, the width $w_i$ of the micro-cracks 500 in the images captured by the apparatus 100 is 100 μm. This advantageously increases the prominence of the micro-cracks 500 to thereby facilitate the detection of the micro-cracks 500 by the apparatus 100.

Without the use of the foregoing oblique arrangement, the micro-cracks 500 as inspected by conventional methods and devices would appear in the images having a width of 5 pixels, which is not sufficiently prominent to be detected.

Furthermore, according to the foregoing mathematical relationship, the width $w_i$ of the micro-cracks 500 contained in the images captured by the apparatus 100 is independent of the actual width of the micro-cracks 500. This means that the apparatus 100 is capable of detecting a 1 μm width micro-crack as easily as a 50 μm width micro-crack.

The apparatus 100 preferably comprises a pair of imaging devices 104, 106 and a pair of light sources 108, 110 for use in creating high contrasting images of the micro-cracks 500 so as to facilitate effective detection of micro-cracks 500 on the solar wafer 114 along the x and y-axes. Realistically, the micro-cracks 500 usually extend randomly in all directions.

The micro-cracks 500 preferably appear as dark lines in the images of the solar wafer 114 captured by the apparatus 100. Alternatively, the micro-cracks 500 appear as bright lines in the same images of the solar wafer 114. The apparatus 100 advantageously create high contrast images of the micro-cracks 500 to facilitate detection thereof.

Figure 6A:
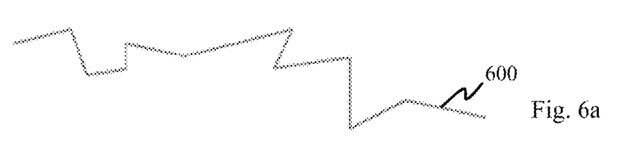
FIGS. 6a to 6c are images of micro-cracks obtained by the apparatus of FIG. 4.
Figure 6B:
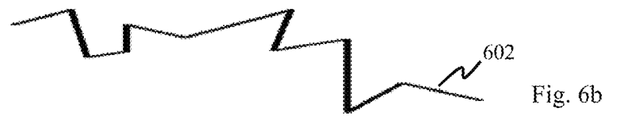
Figure 6C:
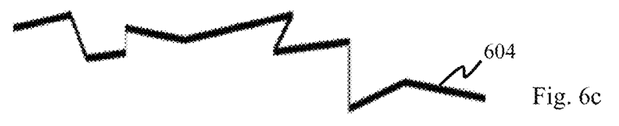

FIG. 6a shows a first view 600 of the micro-crack 500 captured by the apparatus 100 when the first and second imaging devices 104, 106 are positioned perpendicularly with respect to the solar wafer 114. The micro-crack 500 is shown to have a substantially constant width. FIGS. 6b and 6c are respective second and third views of the micro-crack 500 captured by the first imaging device 104 along the x-axis and the second imaging device 106 along the y-axis.

Each of the second and third views 602, 604 shows that the micro-crack 500 therein have varying line widths along the respective crack directions. When either of the micro-crack views 602, 604 is used for inspection purposes, there is a possibility that the micro-crack 500 is not detected as a single crack but is detected as several shorter micro-cracks. In this case, the micro-crack 500 may even escape detection altogether if the micro-crack 500 changes direction too frequently and produces only segments of crack shorter than a control limit set by users of the apparatus 100.

The present invention uses a software application executable in the computer 102 to prevent the micro-crack 500 from being undetected.

Figure 7:
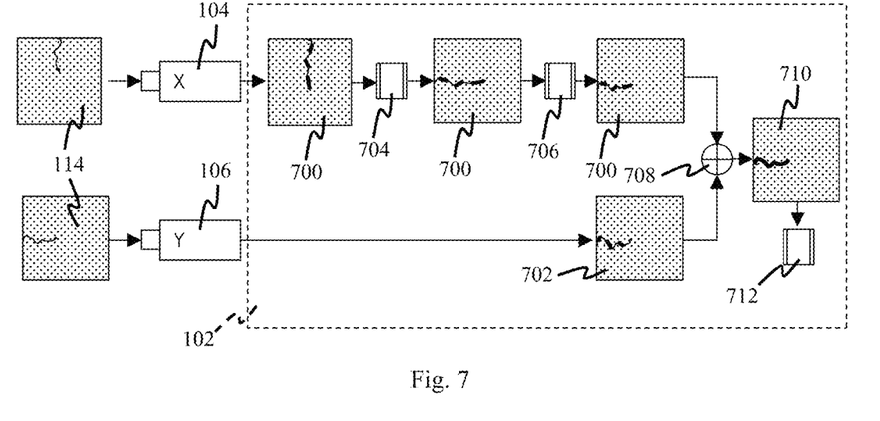
FIG. 7 shows four processes involved in processing images of micro-cracks obtained by the apparatus of FIG. 4.

As shown in FIG. 7, the first imaging device 104 obtains a first image 700 of the solar wafer 114 along the x-axis and the second imaging device 106 obtains a second image 702 of the solar wafer 114 along the y-axis. Both the first and second images 700, 702 are sent to the computer 112 where a first process 704 rotates the first image 700 relative to the second image 702 such that both images 700, 702 have the same orientation.

A second process 706 corrects the rotated first image 700 to positionally register the rotated first image 700 with the second image 702 with respect to perspective and scalar differences, and produces a corrected first image 700. In a third process 708, the corrected first image 700 and the second image 702 are superposed by an arithmetic function, such as a minimum function, to produce a final processed image 710. A fourth process 712 is then used for analysing the final processed image 710 to detect the micro-cracks 500 on the solar wafers 114. The fourth function 712 involves binarization and segmentation functions for analysing and detecting micro-cracks on the final processed image 710.

Figure 8:
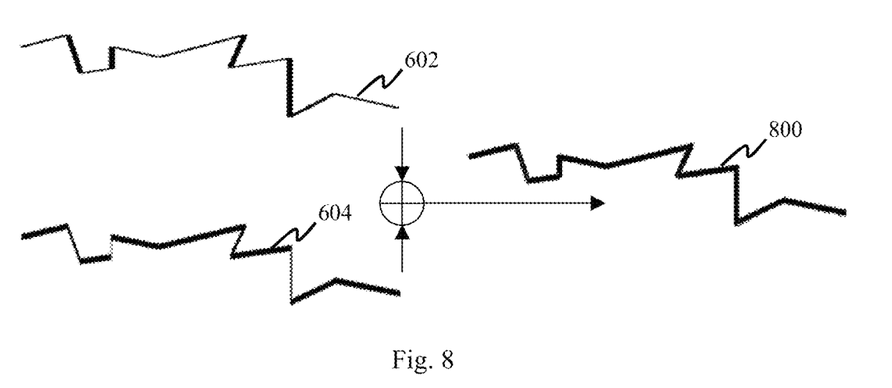
FIG. 8 shows merging of micro-cracks images obtained by the apparatus of FIG. 4.

FIG. 8 shows a micro-crack 800 in the final processed image 710, which is derived by combining the first and second views of FIGS. 6*b* and 6*c*. The micro-crack 800 appears in the final processed image 710 with uniform width and is sufficiently prominent to be detected by the image analysis process.

Figure 9:
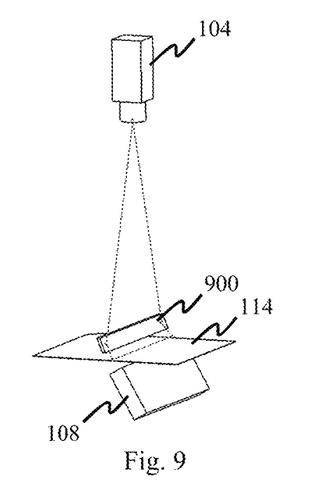
FIG. 9 shows another embodiment of the invention.

FIG. 9 shows another embodiment of the invention. An optical unit or mirror 900 is positioned adjacent to the solar wafer 114 for diverting the infrared light transmitted through the solar wafer 114 towards the first or second imaging device 104, 106. The mirror 900 advantageously allows the first or second imaging device 104, 106 to be positioned at different angles with respect to the solar wafer 114 for receiving infrared light from the first or second light source 108, 110 via the solar wafer 114.

Figure 10:
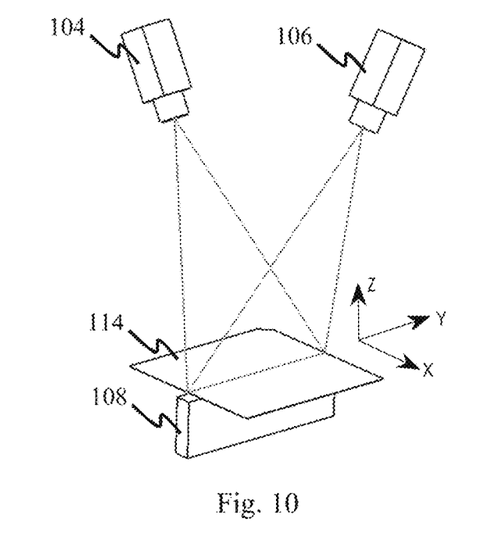
FIG. 10 shows yet another embodiment of the invention.

As shown in FIG. 10, the second imaging device 106 is relocated to a new position such that the first and second imaging devices 104, 106 share a common light source, such as the first light source 108. This arrangement is useful to fulfill certain design constrains of the apparatus 100 or due to space limitation in installing the second portion of the conveyor system 112.

In the foregoing manner, an apparatus and a method for wafer inspection are described according to an exemplary embodiment of the invention for addressing the foregoing disadvantages of conventional method of performing inspection. Although only a few embodiments of the invention is disclosed, it will be apparent to one skilled in the art in view of this disclosure that numerous changes and/or modification can be made to cater to a wider range of hole sizes and heights without departing from the scope and spirit of the invention.

The invention claimed is:

1. An inspection method comprising:
   directing light at a first surface of a wafer along a first direction, the wafer having the first surface and a second surface, wherein the first surface and the second surface are two outward facing surfaces of the wafer and are each substantially parallel to an x-y plane, wherein the second surface is on an opposite side of the wafer as the first surface;
   receiving light transmitted through the first surface of the wafer and emanating from the second surface of the wafer substantially along the first direction for obtaining a first image of the second surface therefrom, the wafer having a crack formed therein, the first image showing the crack as having a first set of line widths;
   directing light at the first surface of the wafer along a second direction;
   receiving light transmitted through the first surface of the wafer and emanating from the second surface of the wafer substantially along the second direction for obtaining a second image of the first surface therefrom, the orthographic projection of the second direction on the x-y plane being substantially perpendicular to the orthographic projection of the first direction on the x-y plane, wherein the second image captures substantially the same surface area of the wafer as the first image, and shows the crack as having a second set of line widths different from the first set of line widths in the first image; and
   constructing a third image from the first image and second image such that the third image shows the crack as having a third set of line widths, wherein the third image is substantially processable for inspecting the crack in the wafer.

2. The inspection method as in claim 1, further comprising directing light towards the first surface of the wafer at substantially an acute angle to the first surface.

3. The inspection method as in claim 1, wherein constructing a third image from the first and second images comprises superposing the first and second images for obtaining the third image.

4. The inspection method as in claim 1, wherein receiving light emanating from the second surface of the wafer substantially along a first direction for obtaining a first image of the first surface therefrom comprises receiving the light transmitted through the wafer and emanating from the second surface of the wafer at an acute angle to the second surface.

5. The inspection method as in claim 1, further comprising providing an optical unit for directing light received from the second surface of the wafer along the orthographic projection of the first direction on the x-y plane.

6. The inspection method as in claim 1, wherein receiving light transmitted through the wafer and emanating from the second surface of the wafer substantially along a second direction for obtaining a second image of the first surface therefrom comprises receiving the light from the second surface of the wafer substantially at a right angle to the second surface.

7. The inspection method as in claim 1, wherein receiving light transmitted through the wafer and emanating from the second surface of a wafer substantially along a first direction for obtaining a first image of the second surface therefrom comprises conveying the wafer along the orthographic projection of the first direction on the x-y plane.

8. The inspection method as in claim 1, wherein receiving light transmitted through the wafer and emanating from the second surface of the wafer substantially along a second direction for obtaining a second image of the second surface therefrom comprises conveying the wafer along the orthographic projection of the second direction on the plane.

9. The inspection method as in claim 1, wherein receiving light transmitted through the wafer and emanating from the second surface of the wafer substantially along a second direction for obtaining a second image of the second surface therefrom comprises rotating the first and second images for spatially registering the first image with the second image.

10. The inspection method as in claim 1, wherein receiving light transmitted through the wafer and emanating from the second surface of the wafer substantially along a second direction for obtaining a second image of the second surface therefrom comprises compensating perspective and scalar differences between the first and second images.

11. The inspection method as in claim 1, wherein constructing a third image from the first and second images comprises merging the first and second images by an arithmetic function.

12. The inspection method as in claim 11, wherein merging the first and second images by an arithmetic function comprises obtaining the third image by a minimum function.

13. The inspection method of claim 1, wherein the first surface is the bottom surface of the wafer, and the second surface is the top surface.

14. An inspection apparatus comprising:
   a light assembly disposed for directing light towards a first surface of a wafer along a first direction and along a second direction, the wafer having a crack formed therein;
   a first imaging device disposed proximate a second surface of the wafer, wherein the first surface and the second surface are two outward facing surfaces of the wafer and are each substantially parallel to an x-y plane, wherein the second surface is on an opposite side of the wafer as the first surface, the first imaging device for receiving light transmitted through the first surface of the wafer and emanating from the second surface of the wafer substantially along the first direction wherefrom a first image showing the crack as having a first set of line widths is obtainable; and a second imaging device disposed proximate the second surface of the wafer for receiving the light transmitted through the first surface of the wafer and emanating from the second surface of the wafer substantially along the second direction wherefrom a second image capturing substantially the same surface area of the wafer as the first image and showing the crack as having a second set of line widths different from the first set of line widths in the first image is obtainable, the first and second imaging devices being inter-configured for disposing the orthographic projection of the first direction on the x-y plane substantially perpendicular the orthographic projection of the second direction on the x-y plane and data couplable with a computer to enable obtaining of the first and second images thereby, wherein a third image is constructible from the first and second images by the computer such that the third image shows the crack as having a third set of line widths, wherein the third image is substantially processable for inspecting the crack in the wafer.

15. The inspection apparatus as in claim 14, wherein the light is directed at the first surface of the wafer and received from the second surface of the wafer at substantially an acute angle thereto.

16. The inspection apparatus as in claim 14, further comprising an optical unit for directing light received from the second surface of the wafer along a direction substantially parallel the orthographic projection of the first direction on the x-y plane.

17. The inspection apparatus as in claim 14, wherein the light received from the second surface of the wafer is received substantially at right angle to the second surface by at least one of the first and second imaging devices.

18. The inspection apparatus as in claim 14, further comprising a conveyer system having a first portion for conveying the wafer substantially parallel the orthographic projection of the first direction on the x-y plane.

19. The inspection apparatus as in claim 18, wherein the conveyer system has a second portion for conveying the wafer substantially parallel the orthographic projection of the second direction on the x-y plane.

20. The inspection apparatus as in claim 14, wherein the computer rotates at least one of the first and second images for spatially registering the first image with the second image.

21. The inspection apparatus as in claim 14, wherein the computer compensates perspective and scalar differences between the first and second images.

22. The inspection apparatus as in claim 14, wherein the computer constructs the first and second images by an arithmetic function.

23. The inspection apparatus as in claim 22, wherein the first and second images are constructed by a minimum function.

24. The inspection apparatus as in claim 14, wherein the light assembly comprises at least one of a first light source and a second light source.

25. The inspection apparatus of claim 14, wherein the first surface is the bottom surface of the wafer, and the second surface is the top surface.

* * * * *